United States Patent
Wlodarski

(10) Patent No.: US 6,361,746 B1
(45) Date of Patent: Mar. 26, 2002

(54) MEDICAL SPECIMEN TOTE

(76) Inventor: Julie Ann Wlodarski, 201 N. Kimrich Cir., Valparaiso, IN (US) 46385

(*) Notice: Subject to any disclaimer, the term of this patent is extended or adjusted under 35 U.S.C. 154(b) by 0 days.

(21) Appl. No.: 09/441,547

(22) Filed: Nov. 16, 1999

Related U.S. Application Data

(60) Provisional application No. 60/108,607, filed on Nov. 16, 1998.

(51) Int. Cl.$^7$ ................................................ B01L 9/00
(52) U.S. Cl. ..................... 422/104; 422/99; 422/102; 62/129; 62/384; 62/371; 200/500; 200/507; 200/751; 200/752
(58) Field of Search ............................... 422/104, 102, 422/99; 62/371, 372, 128, 129, 384, 440, 441; 220/750, 751, 752, 755; 250/500, 507, 750–752, 755; 374/161, 162

(56) References Cited

U.S. PATENT DOCUMENTS

| | | | |
|---|---|---|---|
| 2,393,245 A | 1/1946 | Hadsell | 62/1 |
| 3,163,338 A * | 12/1964 | Gottsegen | 200/752 |
| 3,309,893 A | 3/1967 | Heffler et al. | 62/372 |
| 3,338,068 A | 8/1967 | Piker | 62/398 |
| 3,922,879 A | 12/1975 | Arnold | 62/458 |
| 3,940,249 A | 2/1976 | McClurg | 23/230 |
| 4,145,895 A | 3/1979 | Hjestrand et al. | 62/529 |
| 4,240,547 A | 12/1980 | Taylor | 206/204 |
| 4,266,407 A | 5/1981 | Gibson | 62/371 |
| 4,292,817 A | 10/1981 | Loucks | 62/457 |
| 4,322,954 A | 4/1982 | Sheehan et al. | 62/371 |
| 4,377,077 A | 3/1983 | Granlund | 62/457 |
| 4,425,998 A | 1/1984 | Hof et al. | 206/306 |
| 4,481,792 A | 11/1984 | Groeger et al. | 62/457 |
| 4,498,312 A | 2/1985 | Schlosser | 62/457 |
| 4,530,816 A | 7/1985 | Douglas et al. | 422/1 |
| 4,769,025 A | 9/1988 | Sarstedt et al. | 604/403 |
| 4,788,986 A | 12/1988 | Harris | 128/763 |
| 4,805,188 A * | 2/1989 | Parker | 374/141 |
| 4,850,484 A | 7/1989 | Denman | 206/366 |
| 4,872,563 A | 10/1989 | Warder et al. | 206/634 |
| 4,892,226 A | 1/1990 | Abtahi | 220/412 |
| 4,919,983 A * | 4/1990 | Fremin | 428/35.7 |
| 4,932,533 A | 6/1990 | Collier | 206/569 |
| 4,955,480 A | 9/1990 | Sexton | 206/528 |
| 5,024,067 A | 6/1991 | Maier, III | 62/457.4 |
| 5,181,394 A | 1/1993 | Schea, III et al. | 62/371 |
| 5,208,132 A * | 5/1993 | Kamada et al. | 430/138 |
| 5,215,208 A | 6/1993 | Jackson | 220/516 |
| 5,390,797 A | 2/1995 | Smalley et al. | 206/542 |
| 5,400,610 A * | 3/1995 | Macedo | 62/130 |
| 5,405,012 A | 4/1995 | Shindler et al. | 206/569 |
| 5,417,082 A | 5/1995 | Foster et al. | 62/457 |
| 5,421,172 A | 6/1995 | Jones | 62/457 |
| 5,435,142 A | 7/1995 | Silber | 62/60 |
| 5,546,818 A | 8/1996 | Keefer | 73/863 |
| 5,689,970 A | 11/1997 | Chopas | 62/372 |
| 5,720,555 A * | 2/1998 | Elele | 374/150 |
| 5,786,578 A * | 7/1998 | Christy et al. | 219/720 |
| 5,934,099 A * | 8/1999 | Cook et al. | 62/457.2 |
| 6,126,313 A * | 10/2000 | Schiller | 374/142 |
| 6,174,319 B1 * | 1/2001 | Desnos | 606/133 |
| 6,209,343 B1 * | 4/2001 | Owen | 62/457.2 |

FOREIGN PATENT DOCUMENTS

| | | | |
|---|---|---|---|
| GB | 2183159 | 11/1985 | A61B/5/14 |
| GB | 2321443 | * 7/1998 | G01K/11/12 |

* cited by examiner

*Primary Examiner*—Jill Warden
*Assistant Examiner*—Dwayne K. Handy
(74) *Attorney, Agent, or Firm*—Domenica N. S. Hartman; Gary M. Hartman

(57) ABSTRACT

A medical specimen tote assembly containing a coolant. The assembly is configured with wells sized to individually receive and safely support one or more specimen tubes. At least one of the components of the assembly or a portion thereof is formed to contain a temperature-sensitive material that causes the component or portion to change color when a preselected temperature is exceeded. More preferably, the material causes a color change to occur at or near freezing, so as to indicate if the temperature of the component, and therefore specimens contained by the assembly, is near 0° C. or slightly higher.

17 Claims, 1 Drawing Sheet

MEDICAL SPECIMEN TOTE

CROSS REFERENCE TO RELATED APPLICATIONS

This application claims the benefit of U.S. Provisional Application No. 60/108,607, filed Nov. 16, 1998.

BACKGROUND OF THE INVENTION

1. Field of the Invnetion

The present invention generally relates to medical equipment for handling and temporarily storing materials susceptible to damage if allowed to warm to or above room temperature. More particularly, this invention relates to a medical specimen tote configured to keep blood or other body fluids chilled for an extended period of time.

2. Description of the Prior Art

Blood specimens taken from patients for analysis at some later time are placed in a vial or tube and then chilled to prevent the blood or its components from metabolizing or otherwise undergoing an undesired change. The specimens must safely remain near freezing until they can be analyzed, a typical first step being centrifuging to separate the blood components. The typical method used by phlebotomists and laboratory technicians for keeping blood in adequately chilled has been to fill a Styrofoam cup with ice, and then immerse the blood specimen tubes in the ice. In addition to posing a nuisance to laboratory personnel, this method leaves the specimen tubes vulnerable to breakage by tipping, and does not provide laboratory personnel any feedback as to whether the specimens are properly chilled. While various devices are known for chilling individual containers, such as canned beverages, these devices are unsuitable for handling critical medical laboratory specimens.

SUMMARY OF THE INVENTION

The present invention provides a medical specimen tote assembly containing a coolant. The assembly is configured with wells sized to individually receive and safely support one or more specimen vessels. At least one of the components of the assembly or a portion thereof is formed to contain a temperature-sensitive material that causes the component or portion to change color when it exceeds a preselected temperature. More preferably, the material causes a color change to occur near freezing, so as to indicate if the temperature of the component, and therefore the specimens held by the assembly, is near freezing, i.e., slightly above 0° C.

Prior to usage, the assembly will typically be placed in a freezer to cool the coolant to about 0° C. or less. The coolant is preferably of a type that will remain near 0° C. for an extended period of time once removed from the freezer. The temperature-sensitive material can be relied on to indicate when the assembly and its coolant are sufficiently cold for use. Specimen vessels containing blood or another material susceptible to damage from room temperature conditions can then be placed in the assembly and, as long as the temperature-sensitive material indicates a sufficiently cold temperature exists, will thereafter remain at a safe temperature until removed.

In view of the above, it can be appreciated that the tote assembly of this invention fulfills an important need of phlebotomists and other medical laboratory technicians by saving time, taking up less space and supplying a more reliable means of transporting chilled blood specimens.

Other objects and advantages of this invention will be better appreciated from the following detailed description.

DETAILED DESCRIPTION OF THE PREFERRED EMBODIMENT

Figure 1:
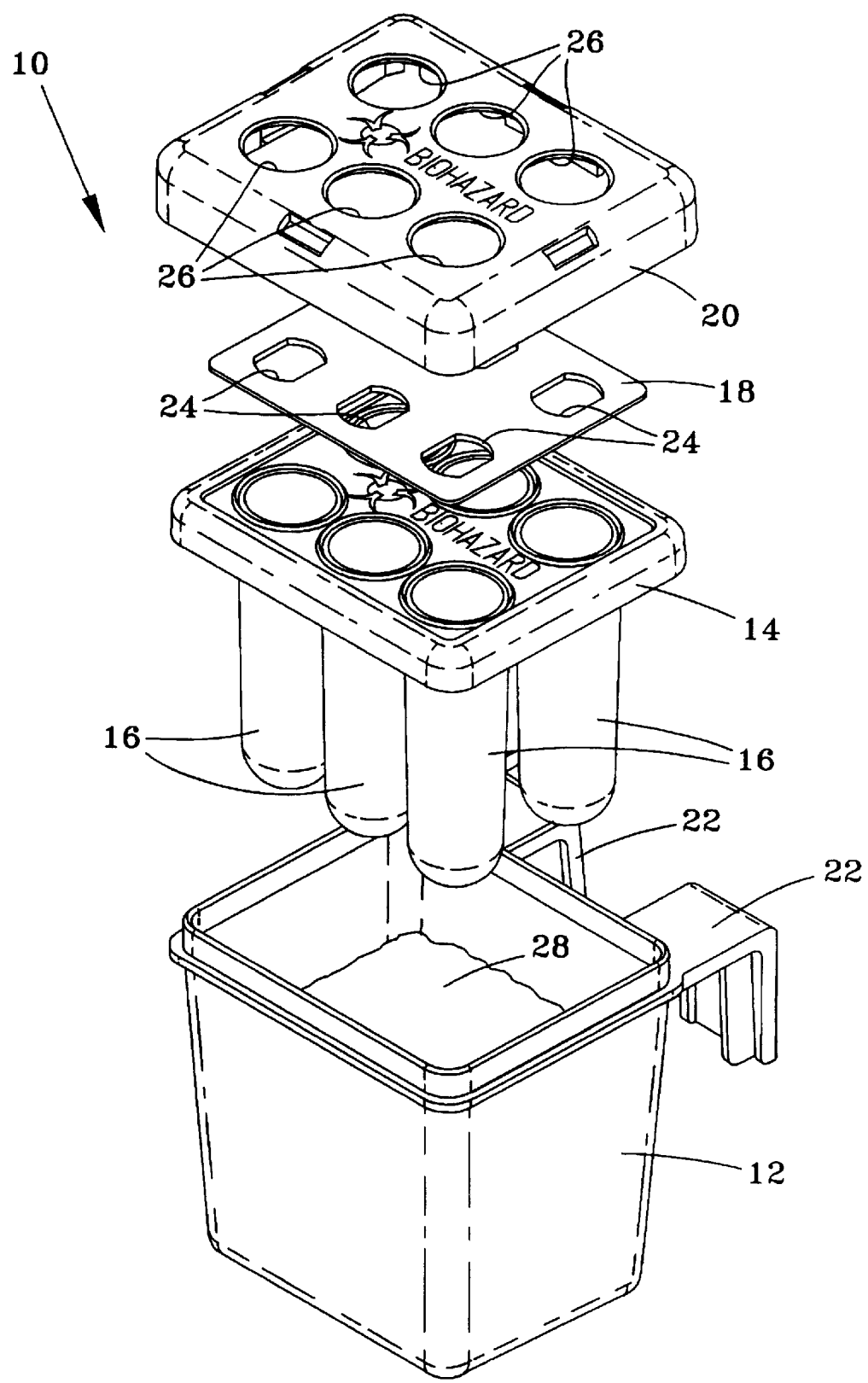
FIG. 1 is an exploded view of a blood tote assembly in accordance with a preferred embodiment of the present invention.

In accordance with the present invention, FIG. 1 shows a blood tote 10 for transporting tubes or other suitable vessels (not shown) containing specimens of blood or other materials susceptible to damage from elevated temperatures. The blood tote 10 is shown is being an assembly composed of a base 12, a body 14 configured with multiple wells 16, a sealing member 18 and a cover 20. The base 12 is shown as including a pair of attachment clips 22 that are sufficiently flexible to enable the blood tote 10 to be attached to various laboratory phlebotomy trays. The wells 16 formed in the body 14 are preferably cylindrical in shape and sized to hold specimen tubes in one or more sizes conventionally used for laboratory procedures. For example, the wells 16 may be sized to accommodate vacuum tubes into which blood is often drawn directly from a patient. Vacuum tubes of this type may have an outer diameter of about $11/16$ inch (about 17 mm) and a length of about 4 inches (about 10 cm). It is foreseeable that a wide variety of other vessels could be accommodated by appropriately modifying the shape and size of the wells 16.

The sealing member 18 is sandwiched between the cover 20 and body 14. The sealing member 18 and cover 20 have openings 24 and 26, respectively, that are aligned with the wells 16 in the body 14, so that specimen tubes can be placed in the wells 16 through the openings 26 in the cover 20. In a preferred embodiment, the wells 16 are greater in length and diameter than the specimen tubes, so that the tubes are suspended within the wells 16. To retain the tubes within the wells 16, the openings 24 in the sealing member 18 are sized and/or shaped so that a portion of the sealing member 18 projects laterally into or over each well 16. The projecting portions of the sealing member 18 serve to cushion the tubes and enable the wells 16 to be sufficiently sized to safely accommodate tubes of differing sizes. For this reason, the sealing member 18 is preferably formed of a resilient material such as a foam rubber. A preferred resilient material for the sealing member 18 is grey silicone, which is approved for medical uses and available from I. B. Moore. In FIG. 1, the openings 24 in the sealing member 18 are shown as having an oblong shape to achieve this feature of the invention, though other shapes are foreseeable. The cover 20 preferably snaps onto the base 12 so as to secure the body 14 and sealing member 18 therebetween.

A cavity exists between the base 12 and body 14, in which a quantity of coolant 28 is contained. The coolant 28 preferably has a relatively high thermal capacitance, so that the coolant 28 generally exhibits a slow rate of temperature increase to room temperature. Distilled water has worked well as the coolant 28, though a variety of suitable gel-type coolants are known and commercially available from a variety of sources. It is foreseeable that still other types of coolant materials could be used, though nonsolid materials are preferred to adequately flow in and around the wells 16. The coolant 28 preferably does not completely fill the cavity so as to allow for thermal expansion.

According to a particular aspect of the present invention, at least one of the components of the blood tote 10 is formed of a material that contains a temperature-sensitive material that causes the component to change color when its temperature rises above a preselected temperature. Depending on the particular application, the preselected temperature will typically be room temperature (about 25° C.) or below. However, for preserving blood specimens, the preselected temperature is preferably at or near 0° C. A suitable temperature-sensitive material for use with this invention is commercially available under the name CHROMICOLOR POLYPROPYLENE CONCENTRATE from Matsui International Company, Inc., and is mixed with a plastic material, such as acrylonitrile butadiene styrene (ABS), from which the component is molded. The component containing the temperature-sensitive material can be any one or more of those shown in FIG. 1. In a preferred embodiment, the base 12 and body 14 are formed to contain the temperature-sensitive material. Alternatively, the temperature-sensitive material may be limited to certain portions of one or more of these components, as long as an acceptable indication of temperature change can be obtained. Using a CHROMICOLOR material identified as Type 07, a color change from blue to clear will occur when the temperature rises above about 5° C. Conversely, the Type 07 material undergoes a color change from clear to blue at about −4° C. when cooled. Other temperature types are commercially available from Matsui International, by which the color change occurs well above and below 0° C. Preferably, the color change is visible from the exterior of the blood tote 10, so that a brief look at the blood tote 10 will indicate whether the tote 10 is sufficiently cold for its intended use. It is foreseeable that other suitable temperature indicators are available from other sources, and provide color indicators other than blue.

Based on the above description, the blood tote 10 of this invention can be placed in a freezer to freeze or otherwise sufficiently chill the coolant 28, and the color indication provided by the temperature-sensitive material can be relied on to indicate when the tote 10 is sufficiently cold for use. In reference to the preferred CHROMICOLOR Type 07 material, a "safe" temperature of about −4° C. or less will be indicated by the color having changed from clear to blue. Thereafter, specimen tubes containing blood can be placed in the wells 16 and, as long as the color indication provided by the temperature-sensitive material indicates that a sufficiently cold temperature exists, will thereafter remain suitably chilled until removed for centrifuging. Again, referring to the preferred CHROMICOLOR Type 07 material, an "unsafe" condition will be evidenced by a color change from blue to clear at about 5° C. Notably, in the preferred embodiment where both the base 12 and body 14 contain the temperature-sensitive material, the base 12 will typically warm at a faster rate than the body 14. As a result, when the base 12 is sufficiently warmed by its environment to become clear (i.e., is above 5° C.), the wells 16 will be visible through the clear base 12, and the color of the wells 16 can still be relied on to indicate whether the tubes within the wells 16 are above or below 5° C.

While the invention has been described in terms of a preferred embodiment, it is apparent that other forms could be adopted by one skilled in the art. For example, while reference is made to the wells 16 being sized to accommodate specimen tubes, the wells 16 can be sized and shaped to accommodate a wide variety of vessels used to contain or store various materials. In addition, while certain temperatures were discussed, lower or higher temperatures could be used as the preselected temperature to be indicated by the temperature-sensitive material. Accordingly, the scope of the invention is to be limited only by the following claims.

What is claimed is:

1. A medical specimen tote comprising:
   a container body having at least a portion thereof that is formed of a temperature-sensitive material that causes the portion to undergo a color change at a preselected temperature;
   at least one well formed in the container body and having an opening surrounded by a rim, the well and the opening being configured to receive a specimen vessel;
   a resilient member protruding laterally inward from the rim of the well and partially across the opening of the well so as to contact retain and suspend a specimen vessel placed in the well; and
   a nonsolid material contained within the container body and surrounding the well for chilling the well.

2. A medical specimen tote according to claim 1, wherein the temperature-sensitive material is dispersed in the container body.

3. A medical specimen tote according to claim 1, wherein the preselected temperature is less than 25° C.

4. A medical specimen tote according to claim 1, wherein the preselected temperature is about 0° C.

5. A medical specimen tote according to claim 1, wherein the preselected temperature is about 5° C.

6. A medical specimen tote according to claim 1, wherein the color change is visible from the exterior of the medical specimen tote.

7. A medical specimen tote according to claim 1, further comprising a cover secured to the container body so as to sandwich the resilient member between the cover and the container body, the cover and the resilient member having first and second openings, respectively, aligned with the well in the body so that a specimen vessel placed in the well must be inserted through the first and second openings and is contacted, retained and suspended within the well only by the resilient member.

8. A medical specimen tote according to claim 1, further comprising means for attaching the medical specimen tote to a phlebotomy tray.

9. A medical specimen tote comprising:
   a base;
   a body assembled with the base and having at least one well having an opening surrounded by a rim, the well and the opening being configured to receive a specimen vessel;
   a coolant surrounding the well for chilling the well; and
   means for causing at least a portion of the base and a portion of the well to undergo a color change when the temperature of the portions of the base and the well rise above a preselected temperature, wherein the color change in the portion of the base is visible from the exterior of the medical specimen tote, and the portion of the base becomes sufficiently clear when above the preselected temperature to render the well visible through the portion of the base and enable ascertaining whether the well is above the preselected temperature as evidenced by whether or not the portion of the well has undergone a color change.

10. A medical specimen tote according to claim 9, wherein the causing means is a temperature-sensitive material dispersed throughout both of the base and the body.

11. A medical specimen tote according to claim 9, wherein the preselected temperature is less than 25° C.

12. A medical specimen tote according to claim 9, wherein the preselected temperature is about 0° C.

13. A medical specimen tote according to claim 9, wherein the preselected temperature is about 5° C.

14. A medical specimen tote according to claim 9, further comprising a resilient member protruding laterally inward from the rim of the well and partially across the opening of the well so as to contact and retain a specimen vessel placed in the well.

15. A medical specimen tote according to claim 9, further comprising means for attaching the medical specimen tote to a phlebotomy tray.

16. A medical specimen tote comprising:

a base;

a body supported by the base and having at least one well suspended within the base, the well having an opening surrounded by a rim, the well and the opening being configured to receive a specimen vessel;

a freezable coolant contained between the base and body and contacting the well;

a cover securing the body to the base, the covering having an opening aligned with the opening of the well in the body;

a sealing member between the cover and the body, the sealing member having an opening therein aligned with the opening of the well and the opening in the cover, the sealing member protruding between the cover and the body and laterally inward over at least a portion of the opening of the well so that only the sealing member contacts, retains and suspends a specimen vessel placed in the well; and means for causing the base and the well to undergo color changes when the temperatures of the base and the well rise above about 5° C., wherein the color change in the base is visible from the exterior of the medical specimen tote, and the base becomes sufficiently clear when above about 5° C. to render the well visible through the base and enable ascertaining whether the well is above about 5° C. as evidenced by whether or not the well has undergone the color change.

17. A medical specimen tote according to claim 16, wherein the causing means is a temperature-sensitive material dispersed throughout both of the base and the body.

* * * * *